United States Patent [19]
Cassou et al.
[11] 4,173,227
[45] Nov. 6, 1979

[54] INJECTING GUN FOR ANIMALS, IN PARTICULAR FOR THE ARTIFICIAL INSEMINATION OF CATTLE

[76] Inventors: Robert E. J. Cassou; Bertrand M. E. Cassou, both of Rue Clemenceau, 61300 L'Aigle, France

[21] Appl. No.: 812,622

[22] Filed: Jul. 5, 1977

[30] Foreign Application Priority Data

| | | | |
|---|---|---|---|
| Jul. 13, 1976 | [FR] | France | 7621438 |
| Nov. 3, 1976 | [FR] | France | 7633107 |
| Jun. 21, 1977 | [FR] | France | 7718992 |

[51] Int. Cl.[2] ........ A61M 1/00
[52] U.S. Cl. ........ 128/235
[58] Field of Search ........ 128/235, 234, 220, 221, 128/224, 237

[56] References Cited

U.S. PATENT DOCUMENTS

| | | | |
|---|---|---|---|
| 3,256,884 | 6/1966 | Hill et al. | 128/235 |
| 3,507,281 | 4/1970 | Cassou | 128/235 |

FOREIGN PATENT DOCUMENTS

| | | | |
|---|---|---|---|
| 72645 | 2/1951 | Denmark | 128/235 |
| 1168607 | 4/1964 | Fed. Rep. of Germany | 128/235 |
| 1525336 | 5/1968 | France | 128/235 |

*Primary Examiner*—John D. Yasko
*Attorney, Agent, or Firm*—Wenderoth, Lind & Ponack

[57] ABSTRACT

The gun is of the type comprising a rigid tubular body provided at one end with a holding head, a flexible sheath surrounding the rigid body and secured by removable means around said head, whereas at the other end it has an injecting orifice around which it comprises an inner reinforcing end member, and a push-rod slidably mounted in the body. The body is slidably mounted in the head and the end member is slidably mounted in the sheath. The end member may be replaced by a solid piston head which is slidably mounted in the sheath and can be removably mounted on the end of the push-rod.

27 Claims, 7 Drawing Figures

INJECTING GUN FOR ANIMALS, IN PARTICULAR FOR THE ARTIFICIAL INSEMINATION OF CATTLE

The present invention relates to injecting guns for animals and in particular for the artificial insemination of cattle, of the type comprising a rigid tubular body having an axial throughway passageway and provided externally at one end with a holding head, a flexible sheath surrounding the rigid body and secured at one end by removable means around the holding head of the body, whereas at the other end, which projects beyond the body, it has an injection orifice around which it comprises an inner reinforcing end member which has a throughway passage and a push-rod slidably mounted in the passage of the body and projecting out of the body adjacent its holding head.

There are known, for example from French Pat. No. 1,467,943, artificial insemination guns of this type which serve to inject doses of semen contained in straws which is disposed in the passage of the body in bearing relation between a shoulder of this passage and the reinforcing end member which, in this case, is fixed, the push-rod serving to urge a plug which closes the straw at the end opposed to the orifice of the sheath so as to inject the semen out of the straw and by way of this orifice, the holding head being moreover permanently fixed to the body of the gun.

Usually there are ten main modes of packing animal semen, namely fresh semen in a tube in the amount of a few milliliters of volume, semen in ampoules of one milliliter, semen in ampoules of one half milliliter, granules which must be diluted into ampoules of serum, kombi-pellets which combine the advantages and disadvantages of semen in ampoules and granules, the doses in French straws of 0.5 ml, doses in French straws of 25 ml, doses in long German straws (minitubes of 90 mm), doses in short German straws (minitubes of 65 mm) and doses in American straws (continental tubes of 56 mm).

An object of the invention is to permit the use of a single gun which thus becomes universal for all these modes of packing.

According to the invention, there is provided a gun of the aforementioned type, wherein the rigid body is freely slidably mounted in the holding head and the reinforcing end member is also freely slidably mounted in the flexible sheath, the sections of the end member and of the body being such that they can bear axially against each other.

In this way it is possible to place the end member at the entrance of the sheath and the straw in this end member, then urge the latter and its straw into position at the end of the sheath by means of the piston body which is made to slide in the holding head on which the sheath has previously been secured. This manner of placing the straw in position has the great advantage of permitting the use of straws of variable lengths, since it does not require the presence of any abutment shoulder inside the body.

In a particularly advantageous manner, the passage in the end member has a stepped diameter, which moreover permits the use of straws of different diameters.

Also advantageously, the passage in the body has two parts of different diameters, so that it is possible to choose the diameter permitting the most effective guiding of the straw to be placed in position.

Also according to the invention, a gun of the aforementioned type is so arranged that the reinforcing end member is replaced by a solid piston head which is freely slidably mounted in the sheath and removably mounted on the end of the push-rod.

In this way, it is possible to employ the gun in the manner of a syringe, which permits carrying out with the same instrument injections which are in any type of packing other than straws, namely tubes, ampoules, granules and kombi-pellets, the latter two being used after dilution of course.

In a particularly advantageous manner, there is employed in this case a sheath of larger diameter which reduces the travel to be given to the push-rod.

Further features and advantages of the invention will be apparent from the ensuing description which is given by way of a non-limitative example with reference to the accompanying drawings in which.

Figure 1:
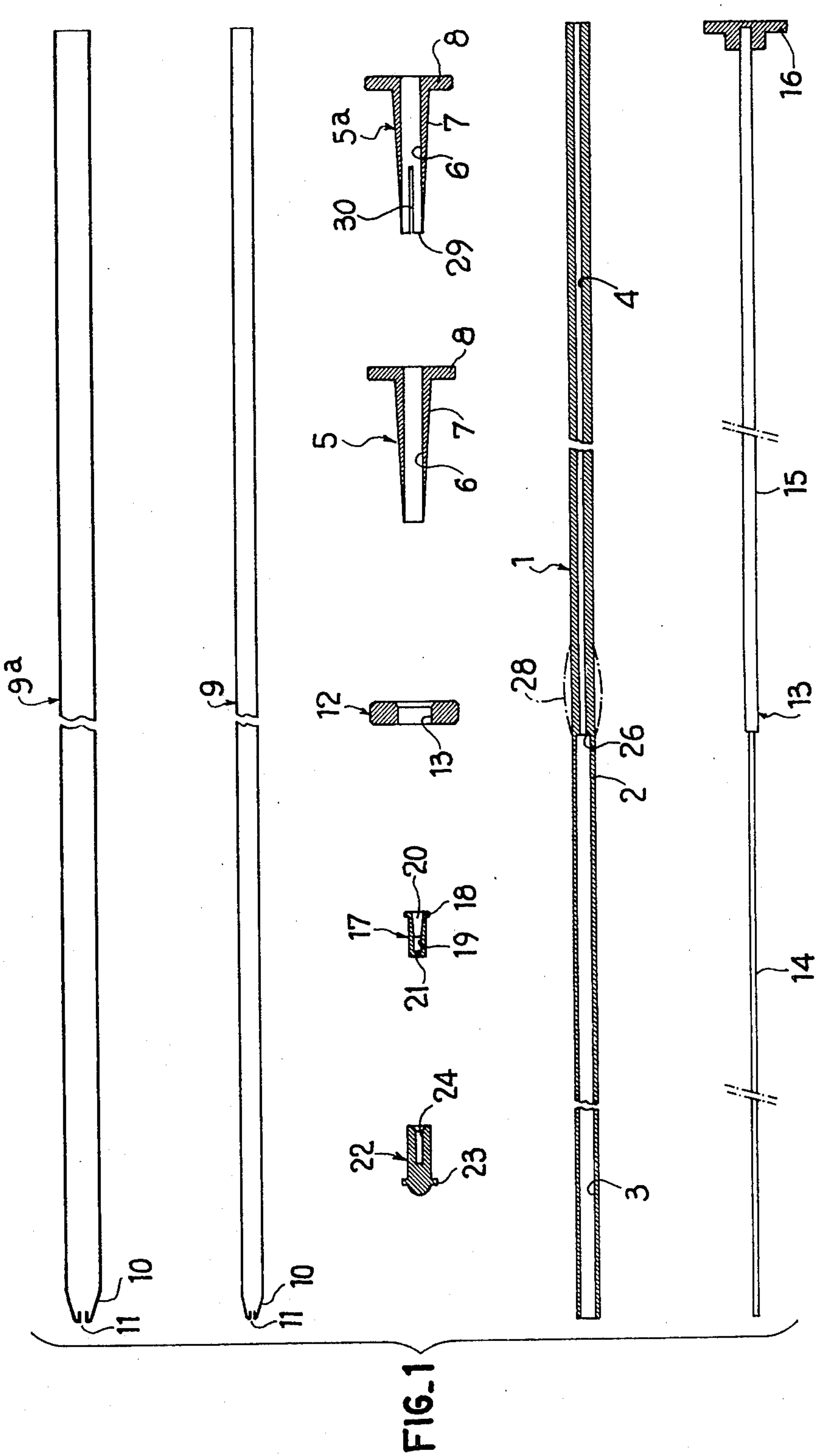
FIG. 1 is an exploded view of the assembly of the different component parts of a gun according to the invention.

As shown in FIG. 1, the gun comprises:

- a long rigid tubular body 1 having an axial passage 2 therethrough and comprising two parts 3 and 4 of different diameters;
- a much shorter holding head 5 having a bore 6 of a diameter corresponding to the outside diameter of the body and a frustoconical outer surface having a small taper 7 and terminating in a flange 8;
- two thin flexible sheaths 9 and 9$^a$ of plastics material having a length roughly equal to the length of the body 1 and having different diameters, both of which diameters exceed the outside diameter of the body and are completely open at one end, whereas they have at the other end a narrowed portion 10 which terminates in a injecting orifice 11;
- a ring 12 whose inner passage 13 terminates in a chamfer and has a diameter intermediate between the extreme diameters of the portion 7 of the head 5;
- a solid push-rod 13 whose length is slightly greater than that of the body 1 and has two portions 14 and 15 of different diameters, the larger corresponding to the smaller diameter of the passage 2 of the body, this rod terminating at its larger end 15 in an actuating head 16 whose diameter is similar to that of the flange 8 of the head 5;
- a reinforcing end member 17 whose outer surface is cylindrical and has a diameter roughly equal to that of the body 1 and terminates at one end in a flange 18 of a diameter corresponding to the diameter of the sheath 9 of the smaller diameter, this end member having extending therethrough a passage in two parts 19 and 20 which are slightly frustoconical and have different sizes, the larger part located adjacent the flange 18 opening directly onto the exterior whereas the narrower part communicates with the exterior by way of a narrow central orifice 21 formed in the end of this end member;

a piston head of flexible material 22 having an outer surface which is cylindrical with a diameter roughly equal to the diameter of the body 1 and having a hemispherical or ogival-shaped end provided with a flange 23 of a diameter corresponding to the diameter of the sheath 9$^a$ of the larger diameter, the piston head having at the other end a blind aperture 24 whose diameter corresponds to the diameter of the part 14 of the smaller diameter of the push-rod 13.

It will be understood that the end member 17 and piston head 22 are not used together but alternatively depending on the type of injection, as will be explained hereinafter.

According to a modification, the solid piston head 22 having a generally cylindrical shape comprises a rigid flange 23 having a diameter slightly greater than the inside diameter of the corresponding sheath.

Figure 7:
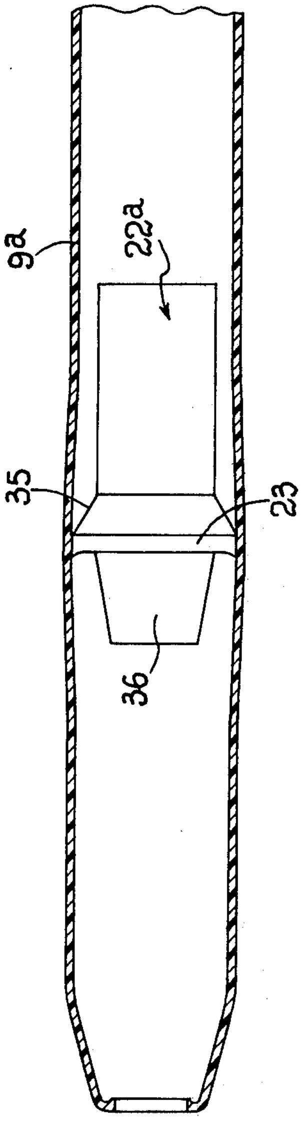
FIG. 7 is a sectional view of a modification of the solid piston head.

FIG. 7 shows a piston head 22$^a$ which is similar to the piston head 22 in that it has a cylindrical outer surface whose diameter is roughly equal to that of the body 1, and has an end provided with a flange 23 whose diameter is slightly larger than the inside diameter of the sheath 9$^a$ of larger diameter.

The flange 23 is rigid and provides the seal by a radial deformation of the sheath upon the passage of the flange therethrough. Consequently, the seal is achieved by the circumferential elasticity of the sheath 9$^a$ and not by that of the flange 23.

In order to obtain the desired stiffness of the flange 23, the latter has a reinforcing member 35 of frustoconical shape connecting its rear face to the cylindrical outer surface and the;end 36 of the flange is preferably frustoconical.

Figure 3:
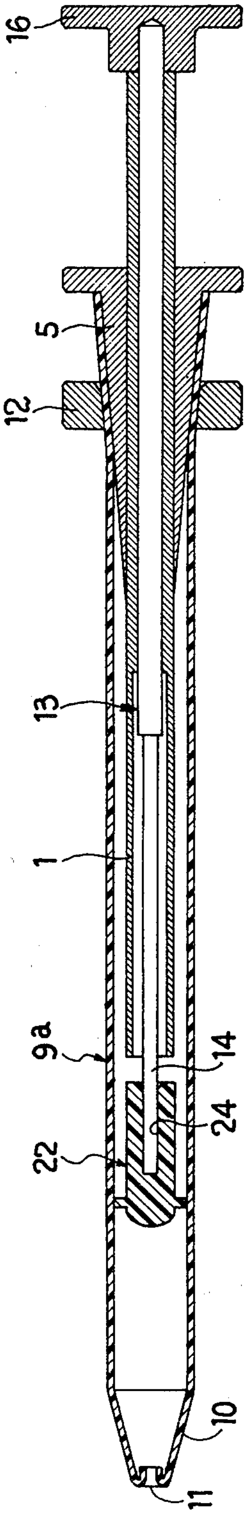
FIG. 3 shows this gun in the assembled state, the relative dimensions having been modified for reasons of clarity.
Figure 2:
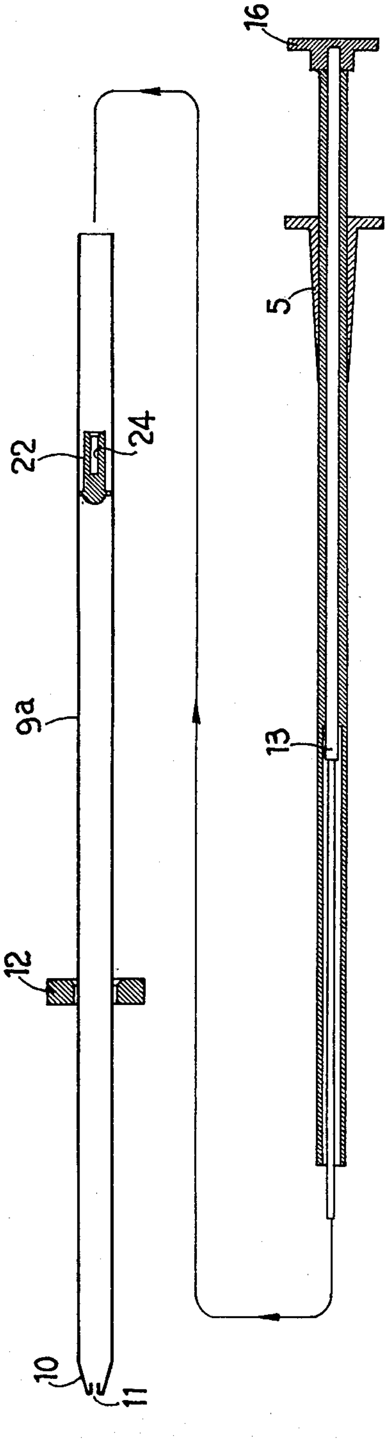
FIG. 2 is a view of a manner of mounting this gun for its use as a syringe.

The gun just described operates in the following manner:

In order to place in position semen which is packed in a way other than in straws (FIGS. 2 and 3), the operator places the holding head 5, provided with its retaining ring 12, firmly in position in the rear end of the sheath 9$^a$. This sheath has at the rear end thereof a slot which facilitates the introduction of the smaller end of the head 5. Beyond this slot, the piston head 22 is in position awaiting the introduction of the push-rod 13 into the blind aperture 24 provided for this purpose. The end of the rod 13 is maintained in this aperture owing to internal suction. This piston head, which is perfectly controlled by the push-rod 13, can advance or more rearwardly in the sheath 9$^a$. In the course of this movement, it performs the function of a sealing piston and draws in or urges back the liquids introduced into the sheath. The operator then presents the push-rod 13 entirely engaged in the body of the gun 1 which is held in any direction, with part 3 or part 4 at the front end, and causes the assembly to enter the sheath in passing along the axis of the holding head 5. The push-rod protrudes from the body by a few millimeters (7 mm for example), which is sufficient to completely fill the blind aperture 24 of the piston head 22. In prolonging the movement until the front end of the sheath 9$^a$ is reached, the operator ensures that the end of the push-rod is fully engaged in the blind aperture. At this moment, the piston head 22 is also fully forward in immediate contact with the front end 10 of the sheath 9$^a$. By plunging the assembly into the liquid to be drawn off, the operator has merely to pull rearwardly the push-rod which pulls rearwardly on the piston head 22 which urges back the gun body 1 which is absolutely free and whose function is limited in this case to stiffening the assembly. The front end of the sheath 9$^a$ is then filed with the liquid to be injected. To expel the liquid, it is sufficient, in order to compensate for the pressure exerted by the thumb on the push-rod head 16, to retain the sheath in front of the ring 12, or on the flange 8 trapped between the index and the middle finger. The hemispherical or ogival front end of the piston head 22 enables it to advantageously fill the whole of the inner part of the front end of the sheath so as to avoid any loss of semen.

Figure 5:
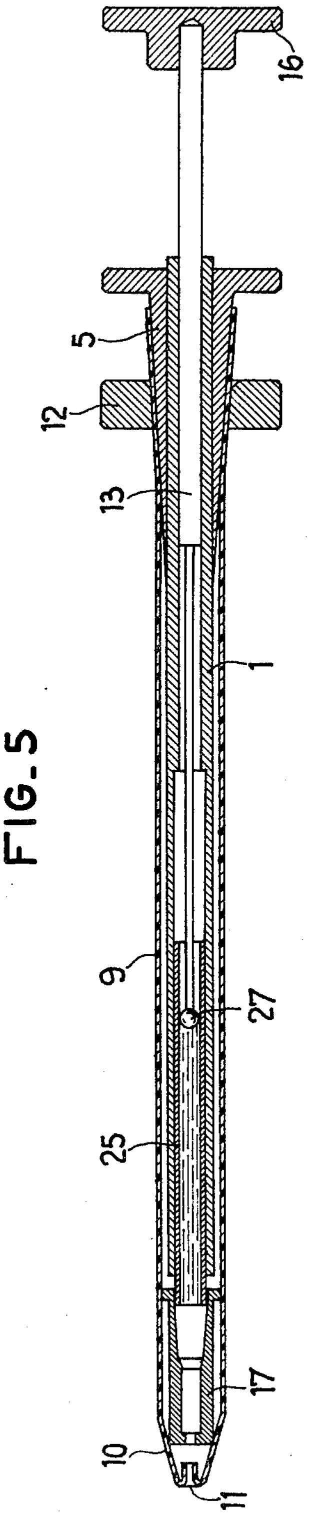
FIG. 5 shows the same gun in the assembled state, the relative dimensions also having been modified.
Figure 4:
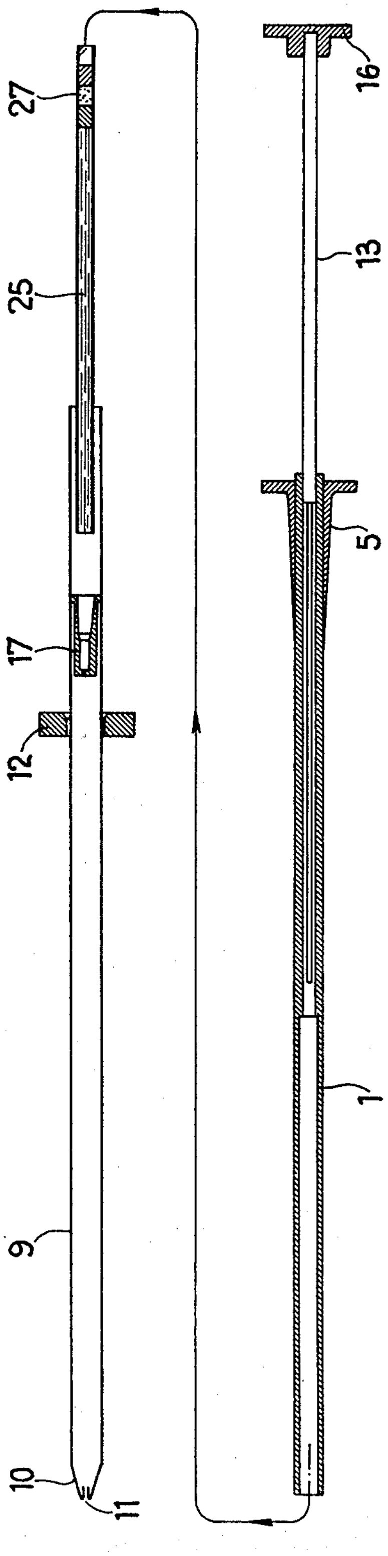
FIG. 4 shows the manner of assembling the same gun for its use with straws.

To place in position semen packed in straws of any type (FIGS. 4 and 5), the operator uses the sheath 9. He presents the straw 25 held between the thumb and the index of the left hand in for example the conical cavity 20 formed in the rear part of the end member 17 whic is retained between the thumb and index of the right hand. By exerting a slight force, the straw is held fast in the cavity 20, the seal achieved being such that the straw can be abandoned by the left hand as it is retained in its cavity. Depending on whether the straw belongs to one of the large groups of straws mentioned hereinbefore, there will be employed for guiding it and protecting it from bending, the end of the gun body 1 whose diameter corresponds best to the diameter of the straw, namely either the end 4 (having an inside diameter of for example 2.2 mm) for straws of 2 mm or the end 3 (having an inside diameter of for example 3.3 mm) for straws up to 3 mm. It will be observed that the length of the straw and the depth of the parts 3 and 4 are of no importance since the seal between the straw and the end member is achieved as soon as the first movement has been effected and not in employing the abutment of the rear end of the straw against the shoulder 26 between the two parts 3 and 4. In holding the sheath loaded with the straw, the operator slips the rear end of the straw in the orifice of the small end of the holding head 5. This head is then placed in position in the sheath 9 which is fixed thereon by the retaining ring 12. The operator then slips the free end of the straw in the end of the gun body 1 whose inside diameter corresponds best to the outside diameter of this straw. The gun body is then slipped in turn on the axis of the holding head and pushed fully into the sheath. This movement permits—without stressing in any way the straw which is immediately capped and fully protected—pushing the end member 17 holding the straw to its final position against the narrowed part 10 of the sheath. The operator then brings the push-rod 13 into contact with the closing element 27 of the straw, namely a plug (cotton, powder, cotton) when it concerns French straws, or a steel ball or a ball of plastics material when it concerns German or American straws. The push-rod then remains in position in the gun body owing to the respective lengths and diameters of this body and this rod which are very close to each other and thus ensures an easy sliding. The insemination operation proper can then be carried out in accordance with the usual rules of procedure by pushing the closing element to the end of its travel by means of the push-rod, so that the semen is expelled from the straw through the end member and the orifice of the sheath.

It will be observed that the sheath 9$^a$ is relatively thicker (wall 0.32 mm thick for example) than the sheath 9 and therefore more rigid and its outside diameter is greater (for example 5.8 mm), so that a column of liquid of 1 ml occupies the least possible length which might adversely affect the rigidity of the end. The sheath 9 is similar but thinner (wall of 0.22 mm for example) and has a smaller outside diameter (4.4 mm for example). The frustoconical parts 19 and 20 of the end member 17 ensure an adherence and a perfect seal with the outer surface of all the types of existing straws. In this particular case, the gun body 1 also serves to position the end member 17. The fact that the body 1 is independent of the holding head 5 permits, depending on the thickness of the straw to be placed in position, employing the adequate end of the body by merely turning the gun body round end for end in the sheath 9. The holding head 5 moreover has such dimensions that they enable it to be introduced and solidly fixed, owing to the retaining ring 12, in the two types of sheath 9 or 9$^a$. The longitudinal and central cylindrical aperture of this head allows the gun body to pass freely, irrespective of the end employed, its inside diameter being slightly greater than the outside diameter of the body (which is for example 3.6 mm), namely for example 3.65 mm. The gun body thus lides rearwardly whatever be the orientation thereof. In general, this body performs, in the particular case of packings other than in straws, solely a stiffening function. In practice, it also guides the push-rod 13. The length of the latter is for example 445 mm whereas the length of the thicker part 15 is about 330 mm.

By way of a modification, one or two slight enlargements 28 on the outer surface of the body 1 may be provided, for example in the vicinity of the shoulder 26 connecting these two parts 3 and 4. This enlargement, obtained by any known means (knurling, crushing, added silver soldering), permits avoiding losing the holding head 5 which slides along the body 1.

According to another modification, in order to avoid the loss of the holding head 5, the latter has one or two axial slots in the part of its length at the end opposed to the flange 8.

This holding head 5$^a$ shown in FIG. 1, is similar to the holding head 5 in that it has a cylindrical bore 6 and a slightly tapering frustoconical outer surface 7 which terminates in a flange 8.

It also has, throughout its thickness but only in roughly ⅓ or ½ of its length, from the end 29 thereof opposed to the flange 8, a narrow axial slot 30, for example of the order of magnitude of 1/10 of the diameter of the bore. This slot permits regulating the opposition to the movement of the head along the body so as to enable the head to be moved by hand as desired by the user, and yet avoid the loss of the head.

According to another modification, in order to avoid the loss of the holding head 5, the latter has in projecting relation inside its bore at least one friction means.

The friction means are preferably disposed on a section of the bore and are composed of flexible material.

According to another feature, the holding head has on its outer frustoconical surface at a slight slope an abutment means for the sheath.

Figure 6:
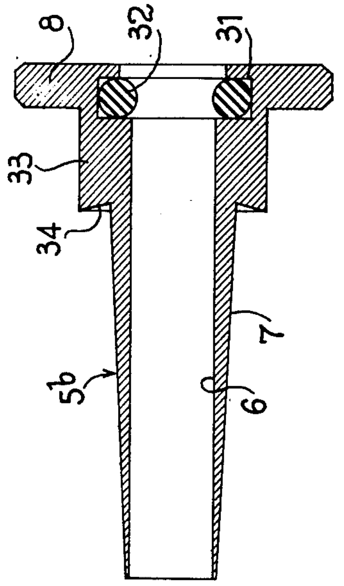
FIG. 6 is a sectional view of a modification of the holding head.

With reference to FIG. 6, the holding head 5$^b$ is similar to the head 5 in that it has a cylindrical bore 6, a frustoconical outer surface 7 having a slight slope and a flange 8.

It also has on the surface of its bore, adjacent the flange 8, an annular groove 31 which receives an O-ring seal 32 which slightly projects from the surface of the bore 6.

The O-ring 32 thus lightly grips the outer surface of the body 1. The light and constant grip obtained permits achieving a displacement of the body 1 in the head, as desired by the user, while avoiding a loss of the head.

The holding head also has on its outer surface, adjacent to the flange, a cylindrical portion 33 coaxial with the bore whose surface 34 by which it is connected to the frustoconical surface 7 forms a shoulder for blocking the sheaths 9 and 9$^a$.

The blocking shoulder provided permits, in addition to positioning the sheaths, ensuring that an excessively violant user does not split the relatively weak end of the sheaths by an abnormally high pressure exerted by the thumb on the actuating head 16.

It must be understood that such an instrument may be employed for injections other than for artificial insemination and usually permits catheterizing certain organs, and in particular the uterus of females. It permits the placing of all types of biological, medical and other products, in addition to live semen.

Having now described our invention what we claim as new and desire to secure by Letters Patent is:

1. An injecting gun for animals, comprising a rigid tubular body defining a throughway axial passage, a holding head defining a bore and provided on the outside of the body adjacent a first end of the body, a flexible sheath surrounding the rigid body, removable means securing a first end portion of the sheath around the holding head of the body, the sheath having a second end portion opposed to said first end portion, which second end portion extends beyond the body and defines an injecting orifice around which orifice there is disposed within the sheath an inner reinforcing end member having a throughway passage, and a push-member slidably mounted in the passage of the body and projecting from the body adjacent the holding head thereof, the rigid body being freely slidably mounted in the holding head and the reinforcing end member being freely slidably mounted in the flexible sheath, the end member and a second end of the body opposed to said first end of the body having such sections that they are capable of bearing axially against each other.

2. A gun as claimed in claim 1, wherein the passage of the end member has a stepped diameter.

3. A gun as claimed in claim 1, wherein the passage of the body has two parts of different diameters.

4. A gun as claimed in claim 1, wherein the push-rod has two parts of different diameters and is freely slidably mounted in the body.

5. An injecting gun for injecting a substance in animals for use either with a straw or tube containing the substance to be injected or without said straw or tube in which latter case the substance to be injected is drawn into the gun before injecting, said gun comprising a rigid tubular body defining a throughway axial passage capable of receiving said straw or tube, a holding head defining a bore and provided on the outside of the body adjacent a first end of the body, a flexible sheath surrounding the rigid body, removable means securing a first end portion of the sheath around the holding head of the body, the sheath having a second end portion opposed to said first end portion, which second end portion extends beyond the body and defines an injecting orifice, a push-member axially movably disposed in the passage of the body and projecting from the body adjacent the holding head thereof, the rigid body being freely slidably mounted in the holding head, at least a part of the passage in the body defining an annular space with the push-member for receiving said straw or tube through which straw or tube the push-member is axially movable, the gun further comprising two component parts only one of which component parts is used at a time, depending on whether the gun is used with or without said straw or tube, a first of said component parts being used when said straw or tube is used and being an inner reinforcing member which is for said second end portion of the sheath and is freely slidably mountable in the sheath and has a throughway passage for said substance, said throughway passage having a part for receiving an end portion of said straw or tube, the end member and a second end of the body opposed to said first end of the body having such sections that they are capable of bearing axially against each other for the purpose of urging the end member toward said second end portion of the sheath by means of the body before use of the gun, a second of said component parts being used when said straw or tube is not used and being a piston head which is slidably mountable in the flexible sheath and mountable on an adjacent end portion of the push-member for axial movement with the push-member in operation of the gun but removable from the push-member when the reinforcing end member is to be used instead.

6. An injecing gun as claimed in claim 5, wherein when the piston head is used, a sheath is used which is of larger diameter than the sheath used when the reinforcing end member is used.

7. An injecting gun as claimed in claim 5, wherein the piston head comprises a rigid flange whose diameter is slightly larger than the inside diameter of the sheath.

8. An injecting gun as claimed in claim 1, wherein the body has an outer surface which comprises at least one slight enlargement acting as an abutment for the holding head.

9. An injecting gun as claimed in claim 1, wherein the holding head has at least one axial slot formed in a part of its length starting at an end of the head.

10. An injecting gun as claimed in claim 9, wherein, in the case where the holding head has a flange at one end, the axial slot extends from an opposite end of the head.

11. An injecting gun as claimed in claim 1, wherein the holding head comprises at least one friction means projecting from the inside of the bore of the holding head.

12. An injecting gun as claimed in claim 11, wherein the friction means are disposed on a section of the bore.

13. An injecting gun as claimed in claim 11, wherein the friction means are of flexible material.

14. An injecting gun as claimed in claim 11, wherein the friction means comprises an O-ring received in an annular groove located adjacent the end having the largest section.

15. An injecting gun as claimed in claim 11, wherein the holding head has a frustoconical outer surface of small taper and further comprises on the frustoconical outer surface an abutment means for the sheath.

16. An injecting gun as claimed in claim 15, wherein the abutment means is in the form of a cylindrical portion which is coaxial with the bore extending from the end of the holding head having the larger section and has a surface connecting it to said frustoconical outer surface which forms a shoulder for blocking the sheath in the axial direction.

17. An injection gun as claimed in claim 5, wherein the body has an outer surface which comprises at least one slight enlargement acting as an abutment for the holding head.

18. An injecting gun as claimed in claim 5, wherein the holding head has at least one axial slot formed in a part of its length starting at an end of the head.

19. An injecting gun as claimed in claim 18, wherein, in the case where the holding head has a flange at one end, the axial slot extends from an opposite end of the head.

20. An injecting gun as claimed in claim 5, wherein the holding head comprises at least one friction means projecting from the inside of the bore of the holding head.

21. An injecting gun as claimed in claim 20, wherein the friction means are disposed on a section of the bore.

22. An injecting gun as claimed in claim 20, wherein the friction means are of flexible material.

23. An injecting gun as claimed in claim 20, wherein the friction means comprises an O-ring received in an annular groove located adjacent the end having the largest section.

24. An injecting gun as claimed in claim 20, wherein the holding head has a frustoconical outer surface of small taper and further comprises on the frustoconical outer surface an abutment means for the sheath.

25. An injecting gun as claimed in claim 24, wherein the abutment means is in the form of a cylindrical portion which is coaxial with the bore extending from the end of the holding head having the larger section and has a surface connecting it to said frustoconical outer surface which forms a shoulder for blocking the sheath in the axial direction.

26. An injecting gun as claimed in claim 1, wherein the passage of the reinforcing end member comprises a part of varying diameter for receiving a straw or tube of various diameters to be engaged therein, the straw or tube containing the substance to be injected by the gun and being received in the passage of said body.

27. A gun as claimed in claim 26, wherein the passage of said body has two parts of different diameters for receiving straws or tubes of different diameters, said body being insertable in the bore of the holding head and in the sheath by either end of said body to suit the diameter of the straw or tube used.

* * * * *